(12) United States Patent
Geng

(10) Patent No.: US 6,594,539 B1
(45) Date of Patent: Jul. 15, 2003

(54) THREE-DIMENSIONAL DENTAL IMAGING METHOD AND APPARATUS HAVING A REFLECTIVE MEMBER

(75) Inventor: Z. Jason Geng, Kensington, MD (US)

(73) Assignee: Genex Technologies, Inc., Kensington, MD (US)

( * ) Notice: Subject to any disclaimer, the term of this patent is extended or adjusted under 35 U.S.C. 154(b) by 0 days.

(21) Appl. No.: 09/616,723

(22) Filed: Jul. 14, 2000

Related U.S. Application Data

(63) Continuation-in-part of application No. 09/282,067, filed on Mar. 29, 1999.
(60) Provisional application No. 60/144,010, filed on Jul. 15, 1999.

(51) Int. Cl.[7] ............................................. G06F 19/00
(52) U.S. Cl. ........................... 700/117; 433/29; 433/37; 264/16; 356/326
(58) Field of Search ........................... 700/163, 59, 96, 700/98, 117, 118, 182, 195; 433/26, 29, 30, 37; 264/16, 17, 18, 19; 356/326, 323, 147

(56) References Cited

U.S. PATENT DOCUMENTS

| | | | |
|---|---|---|---|
| 4,281,931 A | | 8/1981 | Chikama .................... 356/614 |
| 4,575,805 A | | 3/1986 | Moermann et al. ......... 700/163 |
| 4,687,325 A | | 8/1987 | Corby, Jr. ................... 356/309 |
| 4,837,732 A | * | 6/1989 | Brandestini et al. .......... 433/29 |
| 4,881,811 A | | 11/1989 | O'Brien ...................... 356/323 |
| 4,935,635 A | * | 6/1990 | O'Harra ................ 250/559.06 |
| 5,512,036 A | * | 4/1996 | Tamburrino et al. ........ 600/172 |
| 5,675,407 A | * | 10/1997 | Geng .......................... 356/147 |
| 5,702,249 A | * | 12/1997 | Cooper ........................ 433/29 |
| 5,717,455 A | | 2/1998 | Kamewada ................... 348/85 |
| 5,784,434 A | * | 7/1998 | Shieh .......................... 378/191 |
| 6,002,424 A | * | 12/1999 | Rapa et al. .................... 348/66 |
| 6,038,023 A | * | 3/2000 | Carlson et al. ............. 356/326 |
| 6,239,868 B1 | * | 5/2001 | Jung et al. .................... 356/73 |

\* cited by examiner

Primary Examiner—Leo Picard
Assistant Examiner—Chad Rapp
(74) Attorney, Agent, or Firm—Steven L. Nichols; Paul W. Fish; Rader, Fishman & Grauer PLLC

(57) ABSTRACT

An intra-oral imaging system that produces images of a dental surface includes a probe that contains an optical conduit for transmitting light with spatially varying wavelengths for illuminating a dental surface and a camera for receiving light rays reflected from the dental surface. The invention also includes a concave reflector used in conjunction with the probe to increase the field-of-view of the camera, allowing optical coverage of the entire surface of a tooth in a single image.

35 Claims, 3 Drawing Sheets

THREE-DIMENSIONAL DENTAL IMAGING METHOD AND APPARATUS HAVING A REFLECTIVE MEMBER

REFERENCE TO RELATED APPLICATIONS

This application is a continuation-in-part of U.S. application Ser. No. 09/282,067, filed Mar. 29, 1999, and claims the benefit of U.S. Provisional Application No. 60/144,010 filed Jul. 15, 1999.

TECHNICAL FIELD

The present invention relates to intra-oral imaging of dental surfaces, and more particularly to a dental imaging method and apparatus that obtains three-dimensional (3D) imaging techniques to generate models of dental surfaces.

BACKGROUND ART

The accurate and rapid intra-oral measurement of dental surfaces for many purposes, including the production of prosthodontics or dental parts, has been a common goal of dental science. Several systems have been proposed for dental imaging, including a hand-held optical probe using laser and holographic moire techniques and an intra-oral scanner CCD camera that takes multiple images of a tooth illuminated by a striped light pattern.

As is known in the art, tooth reconstruction requires obtaining 3D data that describes the entire surface of the tooth, which includes the chewing surface, the tongue-side area and the cheek-side area up to the gumline. Because a single 3D image taken from a perspective view is usually not sufficient to cover an entire dental surface, it may be necessary to take multiple 3D images of the same dental surface from different viewpoints and then integrate the images together. However, systems that require multiple imaging but cannot obtain multiple images at high speeds require the patient to maintain a fixed position for a long time as the images are taken. Further, image integration is a complex, time-consuming process that does not always provide an accurate representation of the dental surface.

There is a need for a dental imaging system that does not require obtaining multiple images to generate a complete representation of the dental surface.

SUMMARY OF THE INVENTION

Accordingly, the present invention is directed to a dental imaging system that includes an intra-oral probe with a conduit for illuminating the dental surface and a camera for obtaining imaging data as the light rays are reflected from the dental surface. A concave reflector, such as a parabolic or an elliptic reflector, can be used to increase the camera's field of view so that one image can cover an entire dental surface clearly in a single image.

In a preferred embodiment, the intra-oral probe is combined with appropriate data processing and CAD/CAM hardware and software and numerically controlled fabricating equipment, which would allow production of dental parts on a rapid, on-site basis in the dental practitioner's office.

DETAILED DESCRIPTION OF THE PREFERRED EMBODIMENTS

Figure 1:
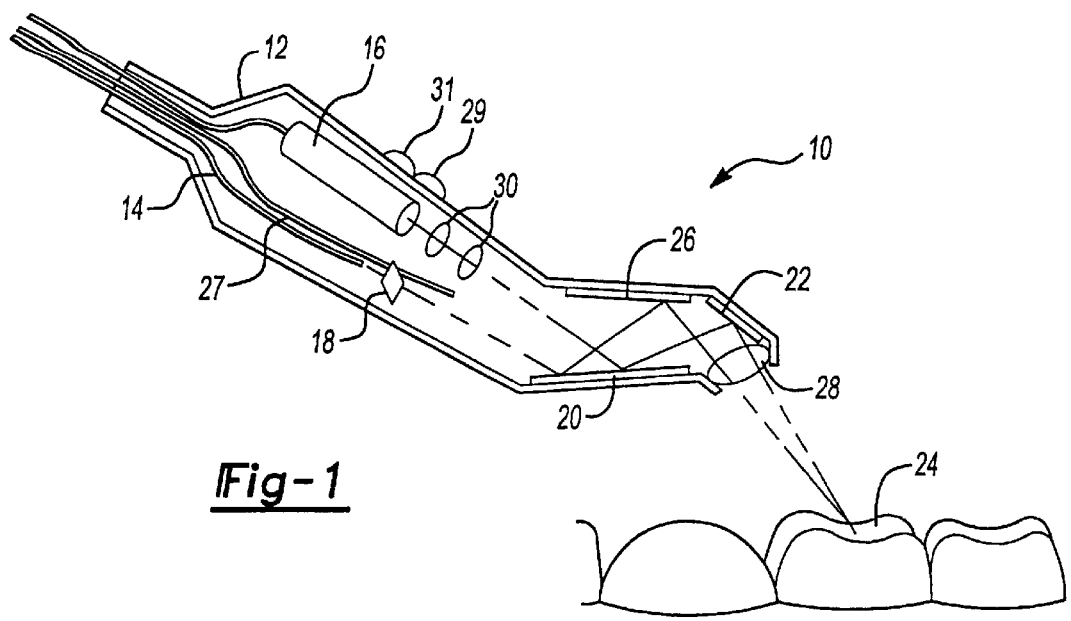
FIG. 1 is a schematic representation of an intra-oral probe used in the present invention.

As shown in FIG. 1, one embodiment of an intra-oral dental probe or camera 10 according to the present invention includes an appropriately-shaped housing 12 that encompasses a fiberoptic light pipe 14 and a CCD camera system 16. Housing 12 may be fabricated from any suitable material, such as a metal or a plastic material; however, for patient comfort, plastic or polymeric materials such as polyethylene or polypropylene are preferred. Similarly, the fiberoptic conduit 14 may comprise a single monolithic light conductor or a bundle of fiberoptic fibers. The fiberoptic configuration is generally preferred as a practical matter because it is less expensive.

A preferred measuring technique used by the present invention is described in U.S. Pat. No. 5,675,407 to Geng, issued Oct. 7, 1997, which is incorporated herein by reference. U.S. Pat. No. 5,675,407 describes a 3D surface profile measuring technique that acquires full-frame 3D images of objects with complex surface geometries at high speed (on the order of 30 frames per second). The term "full-frame 3D image" refers to a 3D image where the value of each pixel in an acquired digital image represents the distance from a camera's focal point to the corresponding point on the object's surface. The purpose, composition and utility of this device are described in detail in U.S. Pat. No. 5,675,407, which is incorporated herein by reference, and therefore the description will not be repeated herein.

A linear variable wavelength filter ("LVWF") 18 is disposed at the outlet of fiberoptic bundle 14. Any commercially available LVWF can be used in the inventive structure. Although this embodiment uses the LVWF 18 to provide spatially varying wavelengths, any device that can provide registered spatial distribution of an energy projection ray corresponding to the ray's wavelength may be used in the inventive system.

Light projected from fiber optic bundle 14 passes through the LVWF 18 and is then reflected by a pair of mirrors 20 and 22 onto the surface of a desired dental structure 24 to be imaged. Light reflected from the surface of the dental structure 24 is then conducted to the CCD device 16 via reflection from mirrors 26 and 20. Appropriate lenses or lens pairs 28 and 30 may be included to focus the image and protect the interior of the housing 12. Note that the specific configuration of the imaging device 10 and the housing 12 as shown in FIG. 1 is not critical to the successful practice of the invention. As long as the housing 12 configuration maintains a fixed relationship between the output end of the fiberoptic bundle 14 and the receiving end of the CCD camera 16 during imaging, the configuration will be acceptable. The projection angles θ, described in U.S. Pat. No. 5,675,407, remain constant and can be readily related to the different spectral wavelengths produced by the light source which serves to define the (x,y,z) coordinates of the 3D image.

Figure 2:
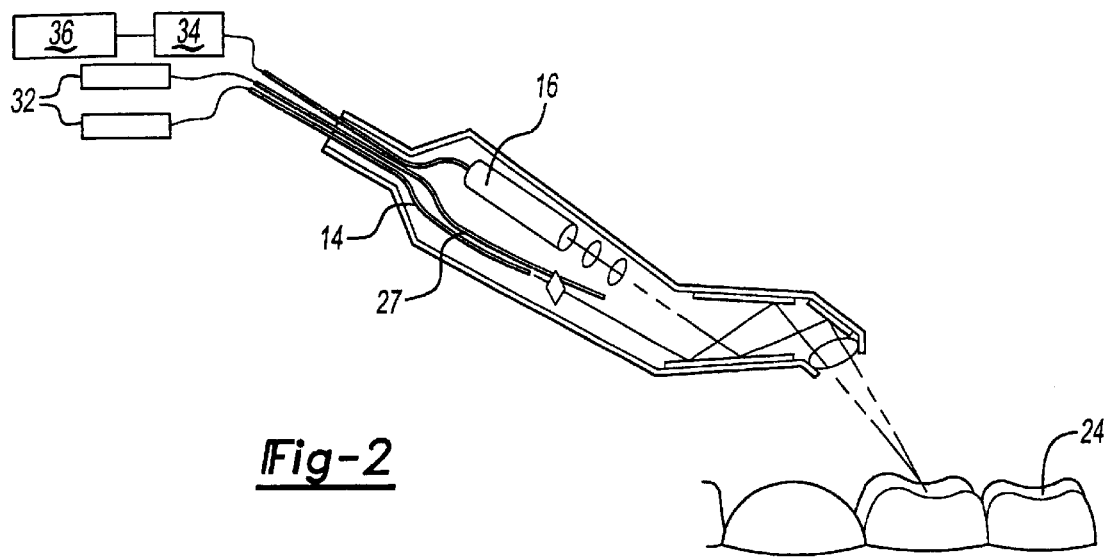
FIG. 2 is a schematic representation of the intra-oral probe shown in FIG. 1 combined with an image processing system.

A more complete view of the imaging system of the present invention is shown in FIG. 2. As shown in this Figure, a light source 32 is connected to the fiberoptic bundle 14. Details about the light source 32 are described in U.S. Pat. No. 5,675,407 patent incorporated by reference herein. Generally, the light source 32 generates a sheet of white light that passes through a cylindrical lens to form a "fan beam" light. This fan beam light then passes through the LVWF 18 to illuminate the dental surface 24 to be "photographed" as described above. Note that although the LVWF 18 is shown in FIGS. 1 and 2 at the exit of fiber optic bundle 14, the LVWF 18 can also be located behind the fiberoptic bundle 14 at the light source 32. The combination of the light source 32 with the LVWF 18 or a similar device produces a bundle of light rays with spatially varying and corresponding wavelengths that are used in the computation and synthesis of the 3D image.

A second fiberoptic conduit 27 acts as a second independent white light source so that the probe 10 can obtain intra-oral images that accurately represent subtle color shadings, shadows, and reflections on the tooth surface. This information is important in building prosthodontics or dental parts to ensure they look natural to the wearer. Obtaining the 3D images by controlling the second light source 27 and the rainbow light using switches 29 and 31 allows the same probe to obtain both 3D and 2D colored images.

To use the inventive dental probe for fabricating dental parts, the CCD camera 16 is connected to an appropriate host computer 34, which preferably contains software for image acquisition, display and processing, 3D computation and data conversion. These computers and the software for accomplishing these operations are known in the art and/or described in the above-referenced U.S. Pat. No. 5,675,407. The host computer 34 is in turn coupled to numerically controlled rapid prototyping, cutting or milling machinery 36. The fabricating equipment can be driven by any known CAD/CAM interface and control software that generates STL, DXF, SLC and HPP files and produces a binary file for driving the control electronics of the fabricating equipment. Any appropriate numerically controlled equipment capable of producing the required dental part may be used as fabricating equipment or machinery 36 in the inventive system.

The inventive system shown in FIG. 2 produces a dental part by exposing a selected dental surface to light emitted from probe 10 and capturing the light reflected from the surface 24 with the camera 16 to obtain a 3D image of the dental surface. The recorded 3D image is then transmitted to the host computer 34 for processing, viewing, archiving, transmission to a distant laboratory, etc. If the user wishes to create a dental part (e.g., inlay, onlay, crown filling, or bridge), the 3D image data is forwarded to a CAD/CAM file, which produces the binary code required to control the fabrication equipment 36. The fabrication equipment 36 then produces the dental part based on the 3D image data obtained from the probe 10.

As explained in the Background Art section, a single 3D image taken by the camera generally will not provide a complete representation of the dental surface because the camera 16 has a limited field-of-view. FIGS. 3 through 8 illustrate several ways in which the inventive system remedies this problem by incorporating the probe 10 shown in FIGS. 1 and 2 with a concave mirror to increase the camera's field-of-view so that an entire tooth surface, including the chewing surface, the cheek-side surface, and tongue-side surface, can be captured in a single 3D image.

Figure 3:
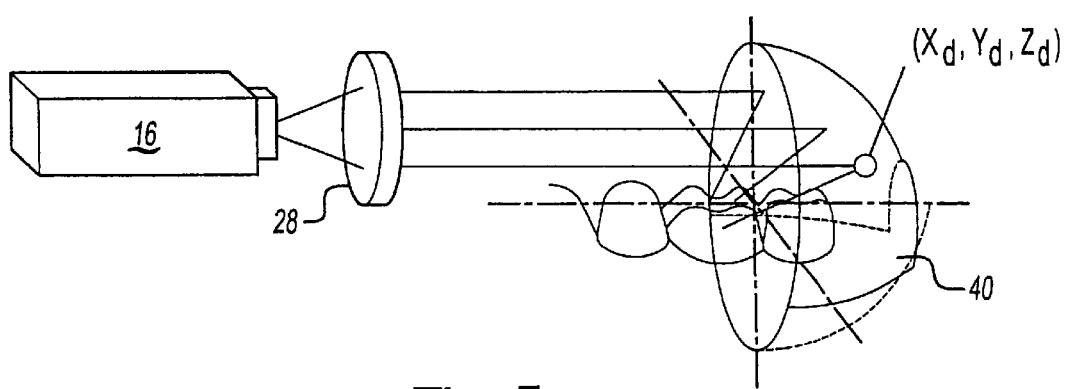
FIG. 3 is a perspective representation of one embodiment of the inventive system.
Figure 4:
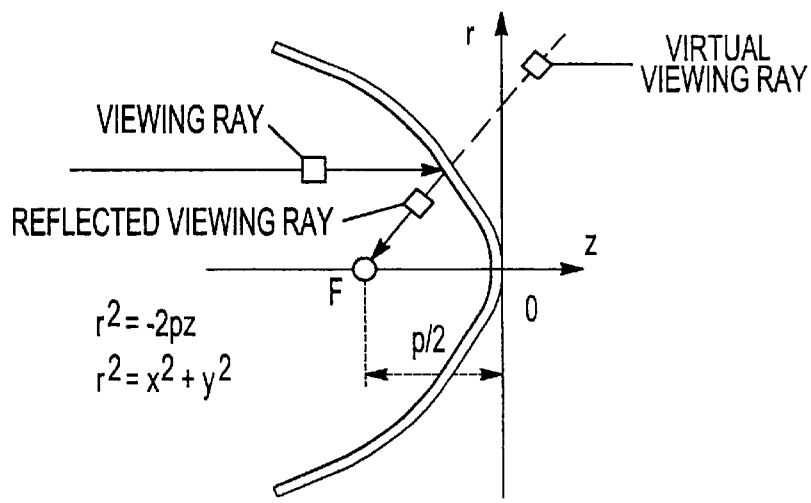
FIG. 4 is an illustration for explaining the reflective characteristics of a reflector used in the embodiment shown in FIG. 3.

FIGS. 3 and 4 shows a configuration where a concave parabolic mirror 40 is used to reflect all viewing rays from camera 16 towards its focal center where the target tooth is placed. The camera 16 is thus able to see a tooth from very large viewing angles, allowing the entire tooth surface to be measured and imaged in a single 3D image. Mathematically, a parabolic surface is defined as:

$$z = \frac{x^2}{a^2} + \frac{y^2}{b^2}$$

If a=b in the above equation, the surface becomes a symmetric surface produced by a parabolic curve rotating around the z axis:

$$r^2 = -2pz, \text{ where } r^2 = x^2 + y^2$$

A fundamental characteristic of a parabolic surface is that all incoming light rays parallel to the z axis will be reflected towards its focus, F, just as if these "virtual" rays are coming from "omni-directions" (e.g. from all angles). This phenomenon for any light ray having a $(x_d, y_d)$ position, its intersection point on the parabolic surface can be calculated as:

$$z_d = \frac{x_d^2}{a^2} + \frac{y_d^2}{b^2}$$

or, for a symmetric case, $$z_d = -\frac{x_d^2 + y_d^2}{2p}$$

Therefore, the spatial orientation of the virtual viewing ray is uniquely defined by $$l = \cos\alpha = \frac{x_d}{\rho}, \quad m = \cos\beta = \frac{y_d}{\rho}, \quad n = \cos\gamma = \frac{z_d}{\rho},$$

$$\rho = \sqrt{x_d^2 + y_d^2 + z_d^2}, \quad l^2 + m^2 + n^2 = 1.$$

Because there is a one-to-one correspondence between the pixel location in an image captured by a camera 16 as shown in FIG. 3 and the $(x_d, y_d)$ spatial position on the parabolic surface, there exists a one-to-one relationship between the pixel location and the spatial orientation of the corresponding viewing ray. This relationship enables us to perform 3D imaging using a camera 16 with the parabolic reflector 40.

Figure 5:
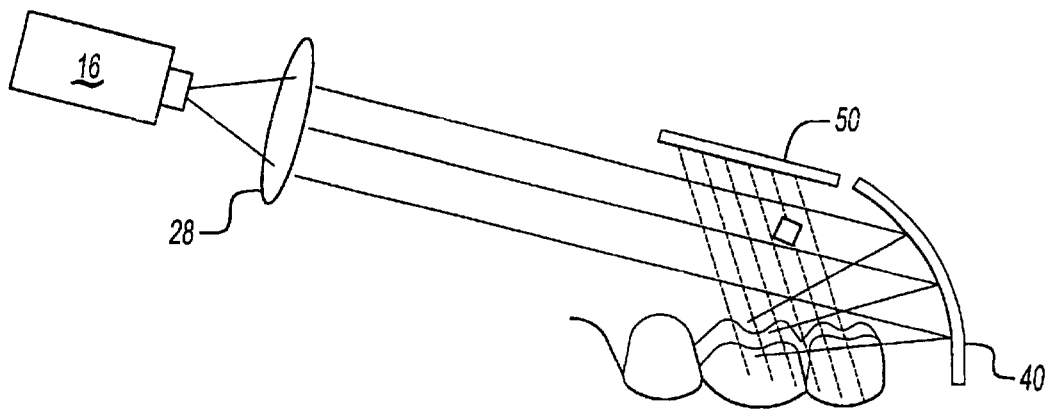
FIG. 5 is a schematic representation of the embodiment shown in FIG. 3.

FIG. 5 shows an embodiment using a rainbow projector 50 in the 3D dental probe with the parabolic reflector 40. A compact rainbow light generator 50 is placed close to the parabolic reflector 40 so that the surface area viewable by the camera 16 will be illuminated by the light having a spatially varying wavelength. The rainbow projector 50 is pre-calibrated so that there exists a one-to-one correspondence between the wavelength on an iso-wavelength light sheet and its spatial orientation. For simplicity, it is assumed that these iso-wavelength light sheets are parallel to each other. The general equation that represents these sheets is given by:

$$x \cos\alpha + y \cos\beta + z \cos\gamma - p_w = 0$$

where (α,β,γ) are the orientation angles of a vector normal to a point on a given surface, and $p_w$ is a variable corresponding to the wavelength.

When using the rainbow projector 50, all the pixels in the image acquired by the camera through the reflector will have the color (wavelength) information on the corresponding surface points due to the divergent light created by the rainbow projector 50. Based on a wavelength look-up-table scheme, the system can determine the spatial location of the iso-wavelength sheet corresponding to the particular color. By solving the two equations above, the system can find the (x, y, z) coordinates for each and every surface point in 3D space. Full-frame 3D images can then be obtained directly at the camera's frame acquisition rate, taking advantage of the increased field-of-view provided by the parabolic reflector 40.

Figure 6:
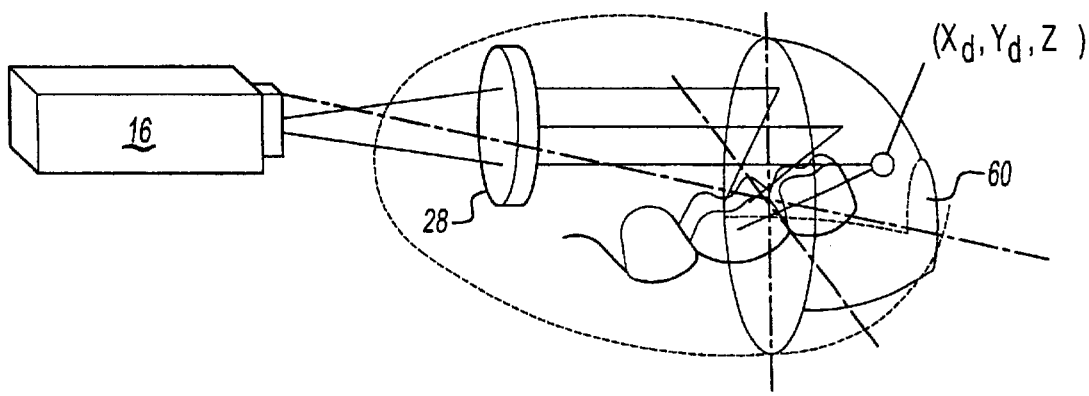
FIG. 6 is a perspective representation of another embodiment of the inventive system.
Figure 7:
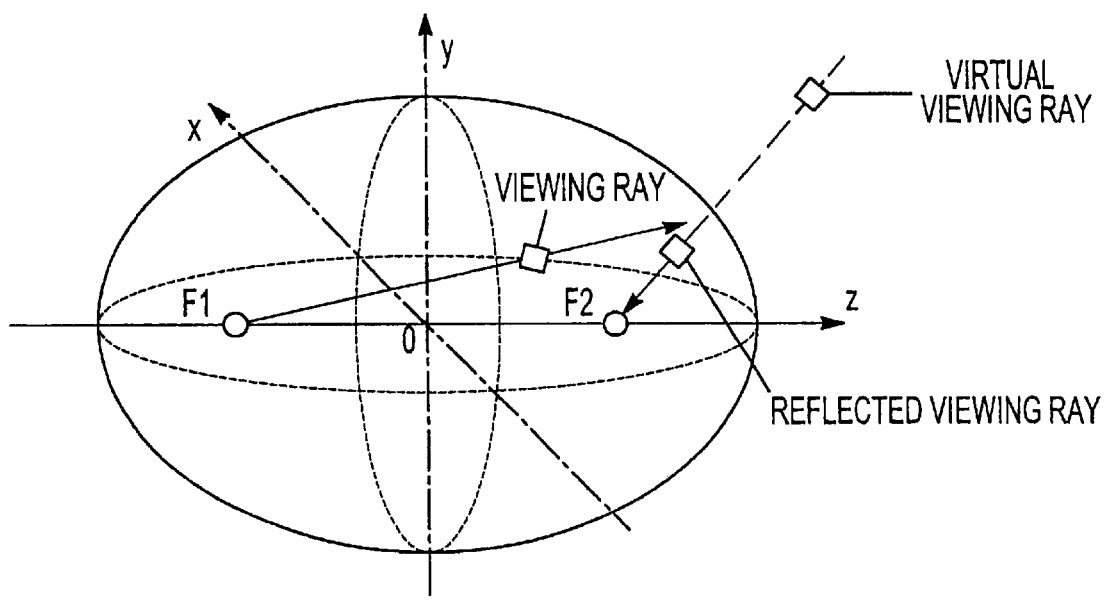
FIG. 7 is an illustration for explaining the surface definition of the mirror used in the embodiment shown in FIG. 6.
Figure 8:
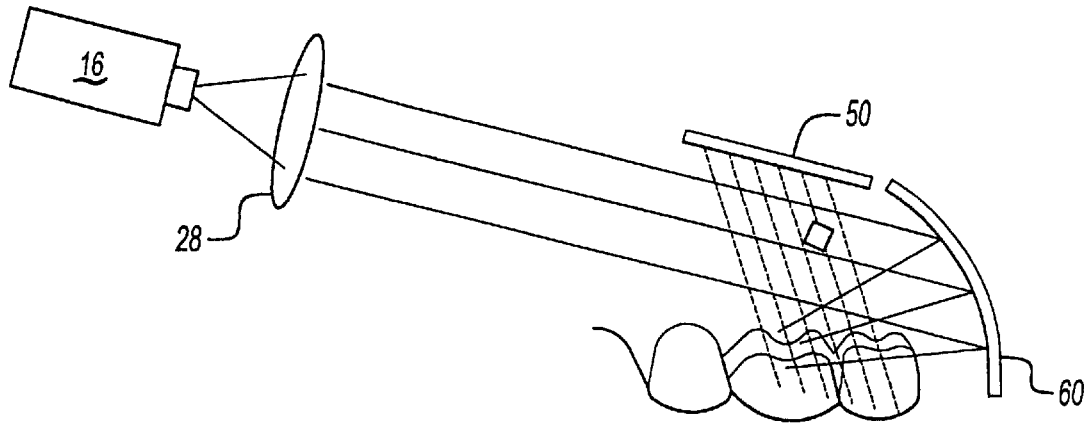
FIG. 8 is a schematic representation of the embodiment shown in FIG. 6.

FIGS. 6 through 8 illustrate an alternative embodiment that replaces the parabolic reflector with an elliptic concave reflector 60, again to achieve a very wide omni-directional field of view for the camera 16. A 3D dental probe 10 using the elliptic reflector 60 will be able to cover the entire surface of a tooth, like the 3D dental probe using a parabolic reflector 50, including the chewing surface, tongue-side surface, and cheek-side surface, in a single 3D image.

FIG. 6 shows a configuration where a concave elliptic mirror 60 is used to reflect all of the viewing rays originating from an optic center of the camera towards the another focal center of the ellipsis where the target tooth to be imaged is placed. The camera 16 is thus able to see a tooth from very large viewing angles to obtain measurements for the entire tooth surface in one image. Mathematically, a parabolic surface is defined as:

$$\frac{x^2}{a^2} + \frac{y^2}{b^2} + \frac{z^2}{c^2} = 1$$

If a=b, the surface becomes a symmetric surface produced by a elliptic curve rotating around the z axis.

A known fundamental characteristic of a elliptic surface is that all rays originating from focal point F1 will be reflected by the elliptic surface towards focal point F2, just as if these "virtual" rays are coming from "omni-directions" (i.e., from all solid angles). For any such light ray with ($x_d$, $y_d$) position, its intersection point on the elliptic surface can be calculated from the following equation:

$$\frac{x_d^2}{a^2} + \frac{y_d^2}{b^2} + \frac{z_d^2}{c^2} = 1,$$

Therefore the spatial orientation of the virtual viewing ray is uniquely defined by $$l = \cos\alpha = \frac{x_d}{\rho}, \quad m = \cos\beta = \frac{y_d}{\rho}, \quad n = \cos\gamma = \frac{z_d}{\rho},$$

$$\rho = \sqrt{x_d^2 + y_d^2 + z_d^2}, \quad l^2 + m^2 + n^2 = 1.$$

Representative diagrams of a rainbow projector using the elliptical reflector are shown in FIGS. 6 and 8, and a diagram illustrating how light rays are reflected from an elliptic surface is shown in FIG. 7.

Since no scanning mechanism or moving parts are needed by the inventive camera system, the mechanical structure and optical design are very simple and reliable. Additionally, a camera of this type is able to provide both 2D and 3D images with registered pixel locations, simplifying data integration and surface feature analysis. The camera 16 can simultaneously generate both numerical data in the form of coordinates for the solid dimensions of the object (i.e. contours) as well as color and shading subtleties for cosmetic considerations. Thus, the camera performs all of the functions of a conventional intra-oral camera to archive and display 2D video images while also providing 3D sensing capability. Further, the inventive system can be easily combined with appropriate image processing and CAD/CAM hardware and software, to provide a unique system for producing dental parts, i.e. inlays, onlays, single unit crowns, and multiple fixed prosthodontics, in a minimum of time and in a minimum amount of space.

It should be understood that various alternatives to the embodiments of the invention described herein may be employed in practicing the invention. It is intended that the following claims define the scope of the invention and that the method and apparatus within the scope of these claims and their equivalents be covered thereby.

What is claimed is:

1. An intra-oral imaging system comprising:
   an optical conduit;
   a light source generating light rays that are transmitted through said optical conduit to illuminate a dental surface;
   a device for converting said light rays into radiation illumination with spatially varying wavelengths prior to illuminating said dental surface;
   a reflector that directs the light rays from said light source to a selected point; and
   an imager for receiving said light rays when said light rays are reflected from said dental surface and for forming a three-dimensional image of said dental surface.

2. The intra-oral imaging system of claim 1, wherein said reflector comprises a concave parabolic reflector.

3. The intra-oral imaging system of claim 1, wherein said reflector comprises a concave elliptic reflector.

4. An intra-oral imaging system comprising:
   an optical conduit;
   a light source generating light rays that are transmitted through said optical conduit to illuminate a dental surface;
   a device for converting said light rays into radiation illumination with spatially varying wavelengths;
   a reflector that directs the light rays from said light source to a selected point;
   an imager for receiving said light rays when they are reflected from said dental surface;
   a second optical conduit for transmitting diverging white light for illuminating said dental surface; and
   a switch for selecting between said optical conduit and said second optical conduit.

5. The intra-oral imaging system of claim 4, wherein said reflector comprises a concave parabolic mirror.

6. The intra-oral imaging system of claim 4, wherein said reflector comprises a concave elliptic mirror.

7. The intra-oral imaging system of claim 1, further comprising a computer coupled to said imager, the computer including software for acquiring, processing and producing three-dimensional images detected by said imager.

8. The intra-oral imaging system of claim 1, wherein said imager comprises a charge coupled device ("CCD") camera.

9. The intra-oral imaging system of claim 1, wherein said device for converting said light rays into light with spatially varying wavelengths comprises a linear variable wavelength filter ("LVWF").

10. The intra-oral imaging system of claim 1, wherein said optical conduit further comprises a housing.

11. The intra-oral imaging system of claim 10, wherein said housing has an outlet with said device for converting said light rays into radiation with spatially varying wavelengths is situated within said housing at said outlet.

12. The intra-oral imaging system of claim 11, wherein said device for converting said light rays into radiation with spatially varying wavelengths comprises a linear variable wavelength filter ("LVWF").

13. The intra-oral imaging system of claim 1, wherein said optical conduit comprises a fiber optic bundle.

14. The intra-oral imaging system of claim 4, further comprising a computer coupled to said imager, the computer including software for acquiring and processing three-dimensional images obtained by said imager.

15. The intra-oral imaging system of claim 14, further including a computer aided design/computer aided manufacturing ("CAD/CAM") interface linked to said computer and a machine for producing dental parts.

16. The intra-oral imaging system of claim 1, further comprising mirrors for conducting said radiation with spatially varying wavelengths from said optical conduit to said dental surface and conducting said light rays with spatially varying wavelengths reflected from said dental surface to a charge coupled device ("CCD") camera.

17. The intra-oral imaging system of claim 4, wherein said optical conduit and said second optical conduit each comprise a fiber optic bundle.

18. An intra-oral imaging system comprising:
    an optical conduit;
    a light source generating light rays that are transmitted through said optical conduit to illuminate a dental surface;
    an imager for receiving said light rays when they are reflected from said dental surface;
    a device for converting said light rays into radiation illumination with spatially varying wavelengths;
    a second optical conduit for transmitting diverging white light for illuminating said dental surface; and
    a switch for selecting between said optical conduit and said second optical conduit; and
    a concave reflector that directs the light rays from said light source to a selected point.

19. The intra-oral imaging system of claim 18, wherein said concave reflector is a concave parabolic reflector.

20. The intra-oral imaging system of claim 18, wherein said concave reflector is a concave elliptic reflector.

21. The intra-oral imaging system of claim 18 wherein said optical conduit and said second optical conduit each comprise a fiber optic bundle.

22. The intra-oral imaging system of claim 18, further comprising mirrors for conducting said light with spatially varying wavelengths from said optical conduit to said dental surface and conducting said light rays with spatially varying wavelengths reflected from said dental surface to a charge coupled device ("CCD") camera.

23. The intra-oral imaging system of claim 18 further including:
    a computer coupled to said imager, the computer including software for acquiring and processing images obtained by said imager; and
    a computer aided design/computer aided manufacturing ("CAD/CAM") interface linked to said computer and a machine capable of producing dental parts.

24. The intra-oral imaging system of claim 4, wherein said imager comprises a charge coupled device ("CCD") camera.

25. The intra-oral imaging system of claim 4, wherein said device for converting said light rays into light with spatially varying wavelengths comprises a linear variable wavelength filter ("LVWF").

26. A method for imaging intra-oral structures, said method comprising:
    transmitting light through an optical conduit to illuminate a dental surface;
    converting said light rays into radiation with spatially varying wavelengths prior to illuminating said dental surface; and
    receiving said light rays when said light rays are reflected from said dental surface to form a three-dimensional image of said dental surface.

27. The method of claim 26, further comprising reflecting said light rays to a particular spot on said dental surface.

28. The method of claim 26, acquiring, processing and producing three-dimensional images from said light rays reflected from said dental surface.

29. The method of claim 26, wherein said converting said light rays into radiation with spatially varying wavelengths is performed with a linear variable wavelength filter ("LVWF").

30. The method of claim 26, further comprising producing dental parts based on said image.

31. A method of imaging intra-oral structures, said method comprising
    transmitting light rays through an optical conduit to illuminate a dental surface;
    converting said light rays into radiation with spatially varying wavelengths;
    transmitting diverging white light for illuminating said dental surface thorough a second optical conduit;
    selectively alternating between illuminating said dental surface with radiation with spatially varying wavelengths from said optical conduit and light from said second optical conduit; and
    receiving said radiation with spatially varying wavelengths and said white light when said radiation or white light is reflected from said dental surface.

32. The method of claim 31, acquiring, processing and producing three-dimensional images from said radiation reflected from said dental surface.

33. The method of claim 32, further comprising adding color to said images based on said white light reflected from said dental surface.

34. The method of claim 31, wherein said converting said light rays into radiation with spatially varying wavelengths is performed with a linear variable wavelength filter ("LVWF").

35. The method of claim 31, further comprising producing dental parts based on said images.

* * * * *